US00PP24118P3

(12) United States Plant Patent

Maillard et al.

(10) Patent No.: US PP24,118 P3

(45) Date of Patent: Dec. 31, 2013

(54) NECTARINE TREE NAMED 'NECTASIA'

(50) Latin Name: ***Prunus persica* L. Batsch**
Varietal Denomination: NECTASIA

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 24 days.

(21) Appl. No.: 13/385,646

(22) Filed: Feb. 29, 2012

(65) Prior Publication Data

US 2012/0227142 P1 Sep. 6, 2012

(30) Foreign Application Priority Data

Mar. 2, 2011 (QZ) ..... PBR 20110559

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — Kent L Bell

(74) *Attorney, Agent, or Firm* — Westerman, Hattori, Daniels & Adrian, LLP

(57) ABSTRACT

A new and distinct variety of yellow nectarine tree, denominated 'NECTASIA', has fruits of very long shelf life without alteration before and after harvesting, and with a semi-sweet orange yellow flesh of high eating quality, with a slightly red pigmentation in the stone cavity and around the stone cavity, and an attractive intense and luminous orange red skin, with a very high percentage of luminous purple red blush. Fruits can be consumed crunchy or melting.

4 Drawing Sheets

Botanical classification: *Prunus persica* L. Batsch.

Variety denomination: 'NECTASIA'.

This application claims priority of Community plant variety right No. 2011/0560 filed on Mar. 2, 2011, which is hereby incorporated by reference in its entirety.

BACKGROUND OF THE NEW VARIETY

The present invention relates to a new and distinct variety of nectarine tree, *Prunus persica* L. Batsch, which has been given the variety denomination 'NECTASIA'. This new tree produces fruit with a long shelf life without alteration both on the tree after growth completion and after harvesting, very good eating quality, semi-clingstone yellow flesh fruit for fresh market in August or in September in the Pyrénées-Orientales department, France. Contrast is made to its parents, 'Nectagala' (U.S. Plant Pat. No. 17,581) yellow nectarine tree and 'Nectachief' (U.S. Plant Pat. No. 19,330) yellow nectarine tree, for reliable description. 'NECTASIA' is a promising candidate for commercial success in that it has very attractive fruits with very long shelf life without alteration before after harvesting.

ORIGIN OF THE VARIETY

The 'NECTASIA' yellow nectarine tree originated in a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTASIA' variety resulted from a pollinated cross between the 'Nectagala' (U.S. Plant Pat. No. 17,581) yellow nectarine tree, which was used as the seed parent, and the 'Nectachief' (U.S. Plant Pat. No. 19,330) yellow nectarine tree, which was used as the pollen parent. 'NECTASIA' was provisionally designated, tested and genetically identified by a genetic profile, under number 05.05.05 NJ ASF 0712 and was registered at the Official Catalogue of the Agriculture Ministry of the French Republic on Nov. 23, 2010 under number 4047121. The 'NECTASIA' variety was obtained by hybridizing and propagated by grafting on a 'Franc Inra Montclar' (non-patented) rootstock. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of nectarine tree blooms at the end of February or early in March in the Pyrénées-Orientales department, France. More particularly, it blooms between February 26$^{th}$ and March 20$^{th}$, generally together with 'Nectagala' (U.S. Plant Pat. No. 17,581).

The first fruit of 'NECTASIA' nectarine tree ripens at mid-August or early in September, generally about 5 days later than 'Nectagala' (U.S. Plant Pat. No. 17,581). More particularly, it approximately ripens between August $8^{th}$ and September $7^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
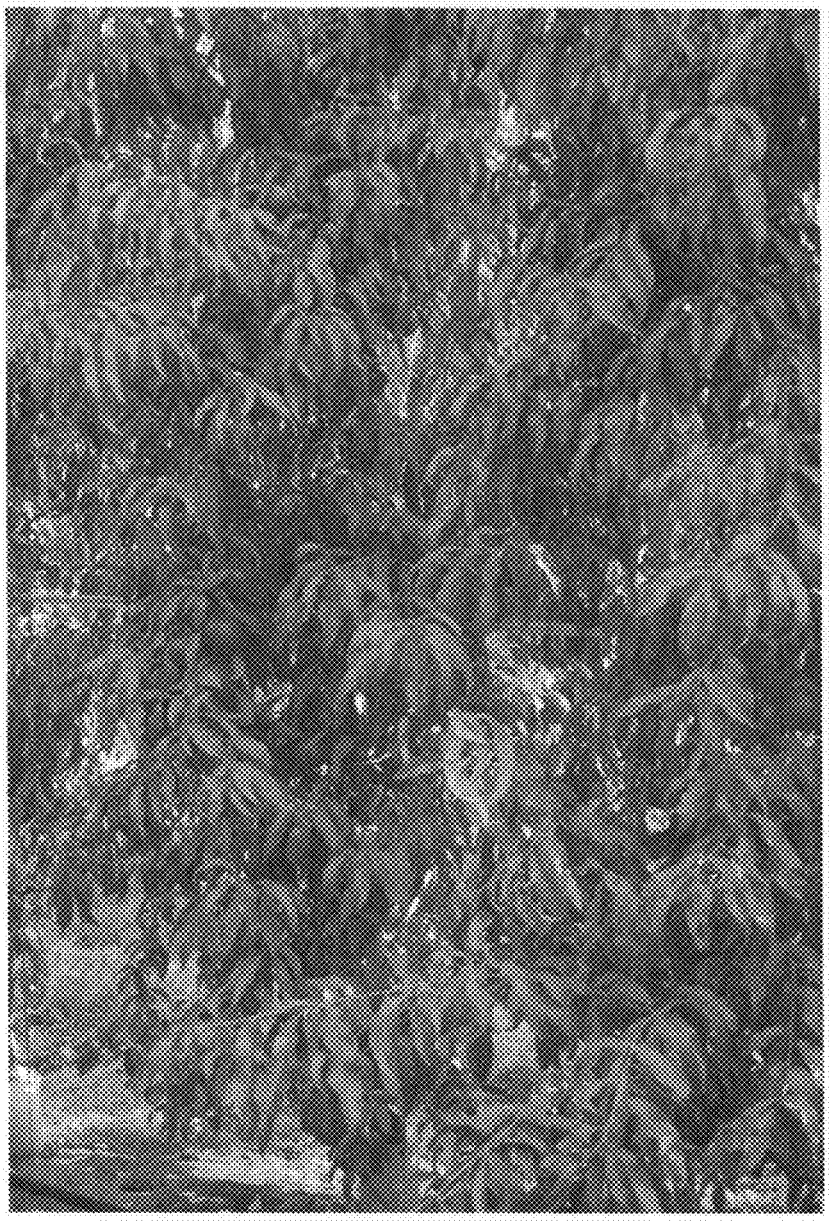
FIG. 1 is a color photograph, which shows a view of a tree of the new variety in orchard, bearing fruits.
Figure 2:
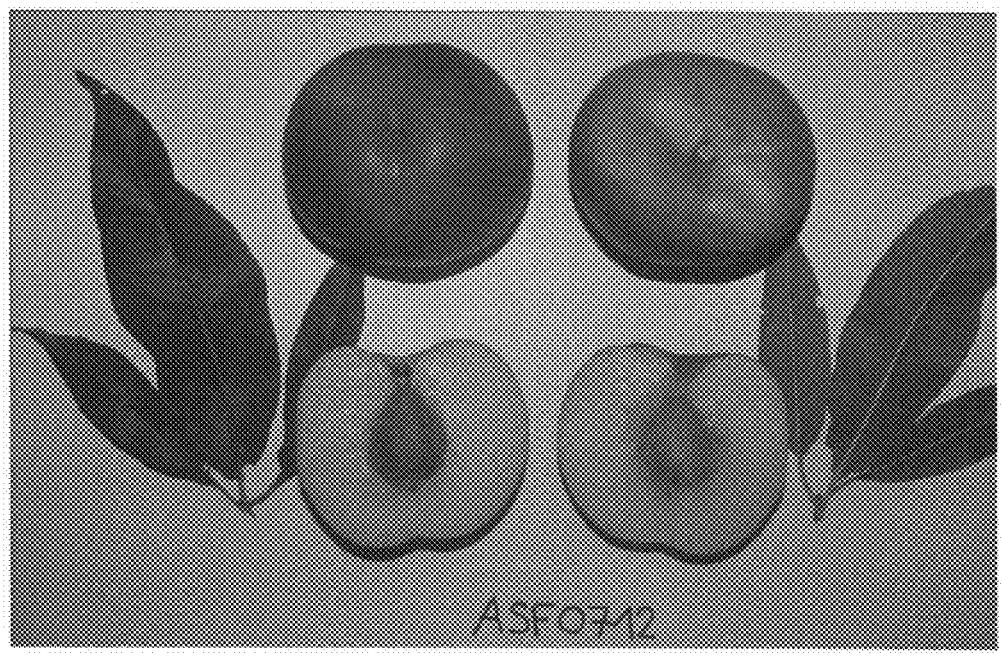
FIG. 2 is a color photograph, which shows two whole fruits and leaves of the new variety, and a third fruit, cut in half with the stone left in one of the halves for depicting the fruit flesh and the stone of the new variety.
Figure 3:
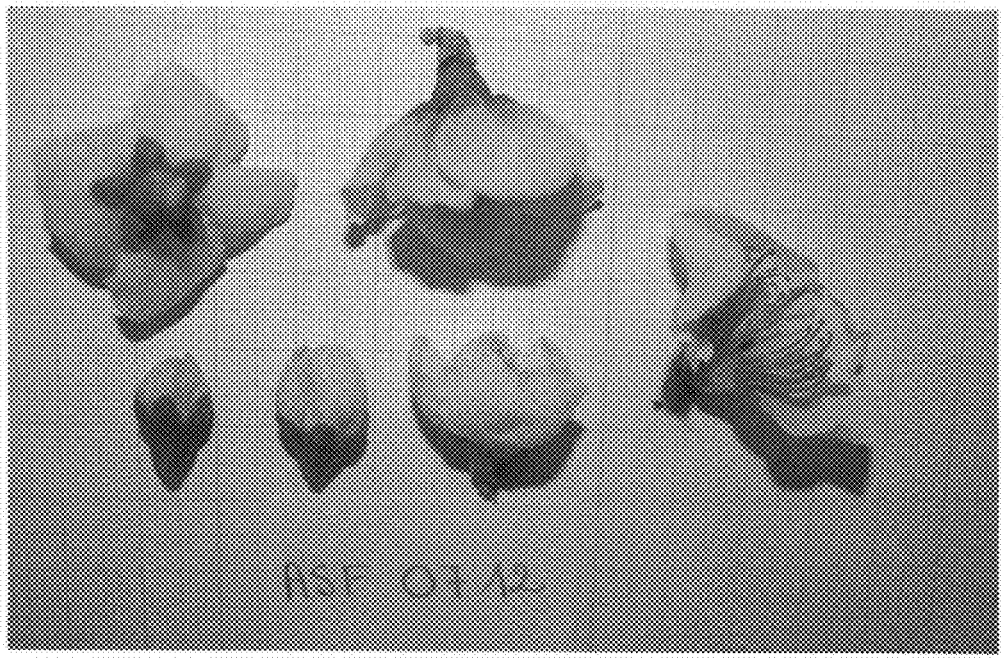
FIG. 3 is a color photograph with reverse and side views of flowers of the new variety, and, with petals removed, reproductive organs of the new variety.
Figure 4:
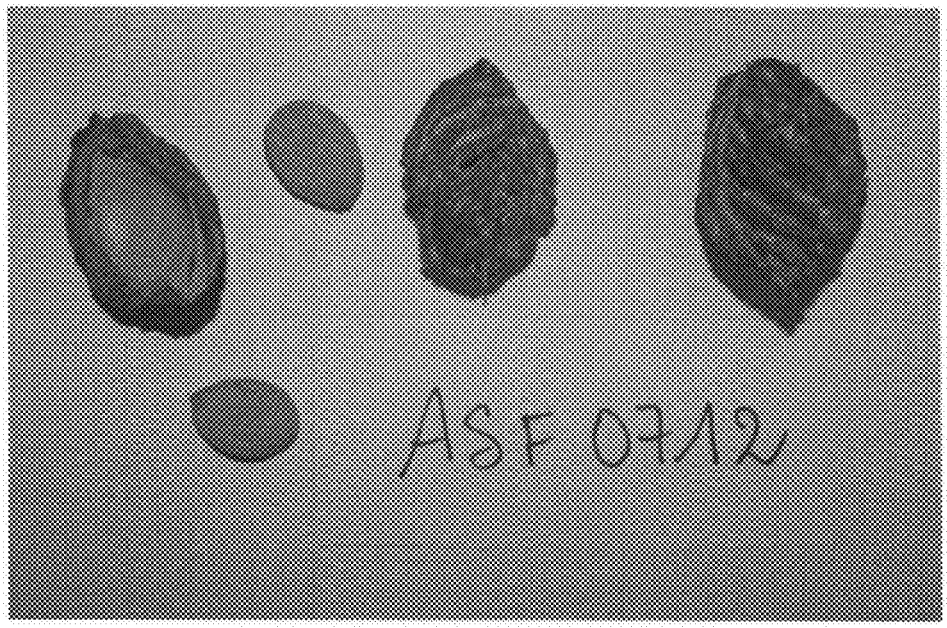
FIG. 4 is a color photograph, which shows different views of the stone and of the kernel.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'NECTASIA' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered medium; flowering begins at the end of February or during March. The type of flower is showy with medium petal size. Petals are medium pink. Leaf glands are present and reniform. The fruit flesh is orange yellow with a slightly red pigmentation, and its skin is very thick, with a luminous purple red blush on an orange red background. The stone is medium size or large size. Fruit taste is semi-sweet, very aromatic and with a high level of sugars.

Compared to 'Nectagala' (U.S. Plant Pat. No. 17,581) yellow nectarine tree, 'NECTASIA' variety has approximately the same time of blooming but ripens approximately 5 days later than 'Nectagala', as set forth above. However, 'NECTASIA' variety produces a higher amount of flowers than 'Nectagala' and 'NECTASIA' has a high rate of fruit set. Shape of 'NECTASIA' fruits is rounder than 'Nectagala' fruits shape and color of 'NECTASIA' fruits is more intense than 'Nectagala' fruits.

The new variety male parent, which is 'Nectachief' (U.S. Plant Pat. No. 19,330), produces yellow nectarines. 'Nectachief' has approximately the same time of blooming with 'NECTASIA' but comparatively ripens 6 weeks earlier than the new variety, which ripens in August, generally during the last two weeks of August. It was chosen as a genitor because of its important and regular productivity and its very attractive fruits presentation, round-shaped, very firm, with a bright orange red color and a homogenous size. Moreover, 'Nectachief' fruits have a semi sweet and very aromatic taste, and a very long shelf life without alteration before after harvesting.

The new variety female parent, which is also the 'Nectagala' (U.S. Plant Pat. No. 17,581) yellow nectarine tree has an interesting level of productivity. 'Nectagala' variety produces yellow nectarines with very high gustative qualities. The fruits of 'Nectagala' have a semi-sweet and aromatic flavour. They are very attractive and homogenous in presentation, with their round form and their bright red coloration on more than 80% of the surface fruit, with an orange red background. 'Nectagala' ripening comparatively begins approximately 4 or 5 days earlier than the new variety's ripening, generally around August $20^{th}$.

DETAILED DESCRIPTION

Referring more specifically to the pomological details of this new and distinct variety of yellow nectarine tree, the following was observed on trees in their third growing season (second year of production) under the ecological conditions prevailing at the orchards located near the town of Elne, Pyrénées-Orientales department, France. All observations have been done on rootstock cultivars. Used rootstocks were 'Franc Inra Montclar' (non-patented) trees. All major color code designations are by reference to The R.H.S. Color Chart (Fourth Edition) provided by The Royal Horticultural Society of Great Britain.

TREE

Size:

*Generally.*—Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised. The tree size is consistently reduced to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered vigorous.

Productivity: Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. The fruit distribution is considered homogenous on mixed branches and spurs having more than 1 year. Thinning of 1 fruit out of 3 or more was necessary for the tree valorisation. Thinning was necessary every year during the years of observation.

Form: The 'NECTASIA' variety has a naturally semi-flared to semi-upright shape.

Density: Considered dense.

Hardiness: The present tree was grown and evaluated in France. The variety appears to be hardy under the central Pyrénées-Orientales department typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

TRUNK

Diameter: Approximately between 8.0 cm and 11.0 cm in diameter when measured at a distance of approximately 20 cm above the soil level.

Bark texture: Considered rough, with lenticels.

Lenticels: Numerous lenticels are present, generally between 5 and 6 lenticels per $cm^2$. The lenticels range in size from approximately 2.0 millimeters to 5.0 millimeters in width, and from 1.5 to 2.0 millimeters in height.

Lenticel color: The outside of lenticels has a silver-grey color (RHS Grey 201 C), whereas the inside is considered brown (RHS Greyed Orange 165 B to 165 C).

Bark coloration: The bark has a light brown color (RHS Brown N 200 C) to a silver-grey color (RHS Grey 201 B to 201 C).

BRANCHES

Size: Mature branches and current season shoots are considered medium for the variety. Mature branches are pruned to a length of approximately 50.0 centimeters.

Diameter: Average as compared to other nectarine varieties. The current season shoots have a diameter from 4.0 to 6.0 millimeters, and mature branches have a diameter from 20.0 to 25.0 millimeters.

Surface texture: Average, wood which is several years old has no furrowed appearance.

Crotch angles: Primary branches are considered variable, but the crotch angles are generally between 70 degrees and 85 degrees from the horizontal axis. This particular characteristic is not considered distinctive of the variety, however.

Current season shoots:

*Surface texture.*—Substantially glabrous.

Internode length: Generally 25.0 millimeters to 30.0 millimeters.

Color of mature branches: Brown (RHS Grey Brown 199 A to 199 B).

Current seasons shoots:

*Color.*—The color of new shoot tips is considered a light yellow-green (RHS Yellow Green 144 A to 144 B) on lower part of new shoot tips, whereas the upper part is colored brown-purple (RHS Greyed Purple 187 A to 187 B).

LEAVES

Size: Considered medium to large for the species. The ratio leaf length/leaf width is 3.93.

Leaf length: Approximately 152.0 to 192.0 millimeters with leaf petiole. The medium length is 173.0 millimeters.

Leaf width: Approximately 40.0 to 49.0 millimeters. The medium width is 44.0 millimeters.

Leaf base shape: Concave.

Leaf form: Lanceolate.

Leaf tip form: Acuminate and small.

Leaf color:

*Upper leaf surface.*—Dark Green (RHS Green 137 A).

*Lower surface.*—A lighter green (RHS Green 137 B to 137 C) than the upper leaf surface color.

Leaf texture: Smooth and glabrous.

Leaf venation: Pinnately veined.

Mid-vein:

*Color.*—Light green, almost yellow (RHS Yellow Green 145 C to 145 D). The color may change with maturity.

Leaf margins: Slightly undulating.

Form: Considered slightly dentate.

Uniformity: Leaves are isolated or grouped by 2 or 3. In this last case, one leaf of normal size is found with one or two smaller leaves (at least 50% smaller).

Leaf petioles:

*Size.*—Considered medium.

*Length.*—About 12.0 millimeters.

*Diameter.*—About 2.0 millimeters.

Petioles color:

*Upper petiole surface.*—Light green (RHS Yellow Green N 144 C).

*Lower surface.*—Light green (RHS Yellow Green N 144 D).

Leaf glands:

*Size.*—Considered medium. Their length is about 1.2 millimeters and their width is about 1.2 millimeters.

*Number.*—Generally 2 or 3 glands per leaf.

*Type.*—Reniform.

*Color.*—On young leaves, leaf gland color is considered a light green (RHS Yellow Green 144 A to 144 B). On older leaves, leaf gland color turns to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variable dimensions. Just before blooming, floral buds are approximately 10.0 millimeters wide and approximately 18.0 millimeters long.

*Color.*—This characteristic is dependent upon the proximity to bloom. At pre-floral stage of development, the bottom of the flowers buds, formed by the sepals, is of purple-brown color (RHS Greyed Purple 183 B to 183 C or Grey Brown Group 199 A); the corolla, formed by the petals, is generally of light pink color (RHS Red Purple 65 A to 65 C). Petals color shows an evolution until the end of flowering.

Hardiness: The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally at the end of February or early in March. The first bloom was observed on Feb. 28, 2003.

Blooming time: Considered medium-season in relative comparison to other commercial nectarine cultivars grown in the Pyrénées-Orientales department, France. The date of full bloom is observed in March, at the middle of the blooming period. The date of bloom varies slightly with climatic conditions and cultural practices. Thus the first full bloom was observed on Feb. 28, 2003. Last observed blooming times were Mar. 5, 2007 then Feb. 26, 2008, then Mar. 2, 2009, then Mar. 20, 2010, then Feb. 26, 2011.

Duration of bloom: Between 10 and 13 days. This characteristic varies slightly with the prevailing climatic conditions.

Flower type: The variety is considered to have a showy type flower.

Flower size: Considered medium. Flower diameter at full bloom is approximately 30.0 to 35.0 millimeters.

Bloom quantity: Considered abundant, approximately between 40 to 45 flowers per meter, with a good distribution and a high rate of fruit set.

Flower bud frequency: Generally 2 flower buds appear per node, occasionally 1.

Petal size:

*Generally.*—Considered medium to large for the species.

Length: Generally about 18.5 millimeters.

Width: Generally about 18.0 millimeters.

Petal form: Round-shaped.

Petal count: Generally 5.

Petal texture: Smooth, sweet and glabrous.

Petal color: Generally, both sides of petals are colored in a medium Pink (RHS Red Purple 65 A to 65 C) and slightly darker at the end of flowering.

Fragrance: Sweet.

Petal claw:

*Form.*—The claw is considered to have a truncated form.

*Length.*—Approximately 1.5 to 1.8 millimeters.

*Width.*—Approximately 1.2 millimeters.

*Color.*—A darker pink than the petal color (RHS Red Purple N 66 B to N 66 C).

Petal margins: Slightly wavy, sinuate.

Petal apex:

*Generally.*—The petal apices are generally dome-shaped.

Flower pedicel:

*Length.*—Considered medium to large and having an average length of approximately 3.0 to 5.0 millimeters.

*Diameter.*—Considered average, approximately 2.0 millimeters.

*Color.*—A brown to light brown (RHS Grey Brown N199 B to N199 C).

Calyx:

*Internal surface texture.*—Smooth and glabrous.

*Color.*—Generally, both surfaces of the calyx are colored in a matt purple brown (RHS Greyed Purple 183 B to 183 C or RHS Grey Brown 199A). Nevertheless, the inner surface of the calyx may be colored in a matt and considered golden orange (RHS Greyed red 178 C to 178 D) color and the outer surface of the calyx may be considered of purple brown (RHS Greyed Purple 183 B to 183 C) color.

Sepals:

*Number.*—Generally 5.

*Surface texture.*—The outer surface has a short, fine pubescent texture.

*Size.*—Medium.

*Length.*—Approximately 5.0 to 6.0 millimeters.

*Width.*—Approximately 4.0 to 5.0 millimeters.

*Form.*—Ovate.

*Color.*—Generally, both surfaces of sepals are colored in a matt purple brown (RHS Greyed Purple 183 B to 183 C or RHS Grey Brown 199A). However, the upper face of sepals sometimes shows a matt and considered golden orange (RHS Greyed red 178 C to 178 D) color, whereas the lower surface of sepals is considered of purple brown (RHS Greyed Purple 183 B to 183 C) color.

*Margins.*—Smooth.

*Apex.*—The apex is round-shaped to emarginated.

Average number of stamens per flower: Approximately 40 stamens per flower.

Anthers:

*Generally.*—Small in length.

*Color.*—Red to orange red color (approximately RHS Greyed Red 178 A Group). The color may evolve with maturity.

Pollen production: Pollen is abundant, and has a yellow color (RHS Yellow Orange 17 B to 17 C) which may evolve with maturity. The present variety is considered auto-fertile (self-pollinating).

Filaments:

*Size.*—Medium length, between 9.0 and 15.0 millimeters in length. Filaments length is generally equal to the pistil's length, if not slightly longer.

Color: Considered light pink (approximately RHS Red Purple 62 C to 62 D or RHS Red Purple 73 A to 73 B). The color evolves during the blooming.

Pistil:

*Number.*—Usually 1.

*Generally.*—Average in size.

*Length.*—Approximately 16.0 to 18.0 millimeters including the ovary which has a size of approximately 1.5 to 2.0 millimeters. Thus, pistil's length is generally equal to or higher than filaments' length, sometimes slightly smaller to filaments in length.

*Color.*—Considered a very pale green (RHS Yellow Green 150 D or RHS Yellow Green 151 D). The color evolves during the blooming.

*Surface texture.*—Non pubescent.

FRUIT

Maturity when described: Very firm ripe condition (shipping ripe).

Date of first picking: Aug. 25, 2003.

Date of last picking: The date of harvest varies slightly with the prevailing climatic conditions. The 'NECTASIA variety has a grouped maturity. The maturity is grouped within 9 to 13 days and the harvest is generally performed in two runs. Last known picking times begin Aug. 14, 2007; then Aug. 18, 2008; then Aug. 20, 2009; then Sep. 7, 2010; then Aug. 8, 2011.

Size:

*Generally.*—Considered large and homogeneous in size.

Average cheek diameter: Approximately 78.0 to 85.0 millimeters.

Average axial diameter: Approximately 70.0 to 78.0 millimeters.

Typical weight: Generally about 250.0 to 280.0 grams. This characteristic is highly dependent upon the prevailing cultural practices, and therefore is not particularly distinctive of the variety.

Fruit form:

*Generally.*—Round or slightly elevated. The fruit is generally uniform in symmetry, viewed from the suture's plane.

Fruit suture: Wide-mouthed and slightly marked, extending from the base to the apex. No apparent callousing or stitching exists along the suture line. Not pointed.

Suture:

*Color.*—The suture has generally a color similar to the whole fruit color. The suture is completely colored with a homogenous purple red (RHS Greyed Purple 187 A to 187 B).

Ventral surface:

*Form.*—Smooth.

Apex: Non-prominent, slightly depressed.

Base: Semi-flared, shallow.

Stem cavity: Average depth of the stem cavity is about 9.0 millimeters. Average width is about 13.0 millimeters.

Fruit skin:

*Thickness.*—Considered very thick and strong, and the adherence of skin to flesh is strong.

*Texture.*—Glabrous.

*Taste.*—Semi-sweet, aromatic, with a high level of sugars.

*Tendency to crack.*—None observed.

Color:

*Blush color.*—This blush color is a luminous purple red (RHS Greyed Purple 187 A to 187 B). The purple red blush covers 85% to 95% of the fruit skin surface on a red orange background (RHS Yellow Group 13 A). The percentage of the blush on the fruit skin surface can vary, and is generally dependant upon the prevailing conditions under which the fruit was grown.

*Ground color.*—The ground color covers 5% to 15% of the fruit skin surface, and is considered red orange (RHS Yellow Group 13 A).

Fruit stem: Medium in length, approximately 7.0 millimeters.

Diameter: Approximately 4.0 millimeters.

Color: Pale green (RHS Yellow Green 145 A to 145 B).

Flesh:

*Ripens.*—Very evenly, homogenously, slowly.

*Texture.*—Very firm, very dense, crunchy, melting, juicy at harvest maturity stage.

*Fibers.*—Not fibrous.

*Aroma.*—Pronounced.

*Eating quality.*—Considered very good, with a high level of sugars.

*Flavor.*—Considered semi-sweet and very aromatic. The Brix is generally superior to 13 degrees and acidity comprised between 6 and 9 meq/100 ml.

*Juice.*—Very juicy at complete maturity.

*Brix.*—Generally superior to 13.0 degrees. This characteristic varies slightly with the number of fruit per tree; prevailing cultural practices; and the surrounding climatic conditions.

*Flesh color.*—Orange yellow flesh (RHS Yellow Orange 15 A to 15 B) with a slightly red pigmentation (RHS Red 53 A to 53 B) into the stone cavity and around the stone cavity, where the pigmentation is star-shaped on approximately 4.0 millimeters.

STONE

Type: Semi-Clingstone.

Size: Considered medium to large for the variety. The stone size varies significantly depending upon the tree vigor, crop load and prevailing growing conditions.

Length: Approximately 34.0 to 39.0 millimeters.

Width: Approximately 23.0 to 26.0 millimeters.

Diameter: Approximately 18.0 to 22.0 millimeters.

Form: Elliptic.

Base: Straight.

Apex:

*Shape.*—The stone apex is pointed, with a small prominent tip.

Stone cavity: Considered medium size, ovate-shaped and dimensions corresponding to the stone's dimensions.

Stone surface:

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved.

Stone color: The color of the dry stone is generally considered purple brown (RHS Greyed Purple 187 A to 187 B or RHS Greyed Red 174 A to 174 B).

Tendency to split: Splitting is absent or very low, depending on climatic conditions between blooming period and stone hardening.

Kernel:

*Size.*—The kernel size is considered medium.

*Length.*—Approximately 18.0 millimeters.

*Width.*—Approximately 13.0 millimeters.

*Thickness.*—Approximately 5.0 millimeters.

*Form.*—Considered oblate and elliptic.

*Pellicle.*—Pubescent.

*Color.*—The kernel skin is an orange brown (RHS Greyed Orange N 167 C to 167 C). The almond, which is the seed of the kernel, is cream-white (RHS Orange White 159 B). The kernel and its embryo are mature at the time of fruit maturity.

Use: The subject variety 'NECTASIA is considered to be a nectarine tree with a semi-late season maturity, and which produces fruits that are considered firm, attractively and intensely colored. Fruits have a semi-sweet taste and are excellent for uncooked consumption, crunchy or melting and juicy when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruits have a slow maturation and a long shelf life both on the tree after growth completion and after harvesting without alteration. After harvest, fruits are well preserved more than 4 weeks after harvest at 2.0 degree Celsius.

Shipping quality: Considered very good. The fruit of the new yellow nectarine variety showed minimal bruising of the flesh or skin damage after being subjected to normal harvesting and packing procedures. Its resistance to handling during harvest and packing and its long shelf life without alteration after harvest easily permit 3 weeks to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of yellow nectarine tree as illustrated and described, characterized by fruits of very long shelf life without alteration before and after harvesting, and with a semi-sweet orange yellow flesh of high eating quality, with a slightly red pigmentation in the stone cavity and around the stone cavity, and an attractive intense and luminous orange red skin, with a very high percentage of luminous purple red blush.

* * * * *